United States Patent [19]

Bowald

[11] Patent Number: 5,141,491
[45] Date of Patent: Aug. 25, 1992

[54] DEVICE FOR CUTTING VENOUS VALVES
[75] Inventor: Staffan F. Bowald, Almunge, Sweden
[73] Assignee: Medical Innovation AB, Sweden
[21] Appl. No.: 573,151
[22] PCT Filed: Jan. 27, 1989
[86] PCT No.: PCT/SE89/00024
§ 371 Date: Sep. 14, 1990
§ 102(e) Date: Sep. 14, 1990
[87] PCT Pub. No.: WO89/06936
PCT Pub. Date: Aug. 10, 1989

[30] Foreign Application Priority Data
Jan. 27, 1988 [SE] Sweden .................. 8800244

[51] Int. Cl.⁵ .................................. A61B 17/32
[52] U.S. Cl. .................................. 604/22; 606/159
[58] Field of Search .................. 606/159, 160, 170; 604/22

[56] References Cited
U.S. PATENT DOCUMENTS
3,525,339 8/1970 Halligan .................. 606/159
4,493,321 1/1985 Leather .................. 128/305

FOREIGN PATENT DOCUMENTS
86048 8/1983 European Pat. Off. .......... 606/159
0170969 2/1986 European Pat. Off. .
0248761 12/1987 European Pat. Off. .

Primary Examiner—Michael H. Thaler
Attorney, Agent, or Firm—Bacon & Thomas

[57] ABSTRACT

A device for cutting venous valves includes a support member adapted to be inserted into a vein and having a fore, rounded insertion end and a rear end provided with valve cutters, the valve cutters having a cutting edge or edges extending substantially transversely to the member and being directed in the backward direction of the support member to cut venous valves when the support member is moved in the backward direction. A possibly branched fluid duct extends from an inlet centrally disposed at the rear end of the support member to at least one outlet located ahead of the valve cutters, and the inlet is connected or connectable to a fluid supply through an at least slightly flexible conduit.

8 Claims, 1 Drawing Sheet

DEVICE FOR CUTTING VENOUS VALVES

BACKGROUND OF THE INVENTION

The present invention relates to an improved device for cutting venous valves.

A common method for remedying circulation disorders, particularly in the lower limbs, due to an artery whose function has been seriously reduced by, e.g., calcification consists in the application of a bypass or shunt around the impaired arterial portion by means of a suitable vein.

Since the flow in the shunt will be opposite to the normal flow direction in the vein, it is necessary to either take out and reverse the vein or remove the venous valves which have the function of non-return valves and otherwise would prevent the flow in the arterial flow direction. Such cleaning of the veins from valves is currently usually performed by means of a so-called valvulotome, which in one form consists of a generally cylinder-shaped body, the fore end of which is rounded to facilitate its insertion into and avoid damage to the vein, and the rear end of which is provided with cutting knives arranged substantially transversely to the axial direction. The valvulotome is inserted through a distal incision into the vein and advanced manually the desired distance in the passage direction of the valves. When the valvulotome is successively drawn back by means of a wire attached to the rear portion thereof, the venous valves will close and be cut off by the cutting knives. Another form of valvuotome is an angled knife which is inserted into the vein and hooked to the valve for cutting it off.

The above described valvulotomes have, however, some disadvantages. On one hand, it is not always ensured that the venous valves are held sufficiently stretched or closed when the valvulotome is drawn back for the valves to be cut to the required extent, and, on the other hand, it may sometimes occur that the vein will spasmodically contract around the valvulotome — spasm — with the result that the blood vessel wall may also be damaged.

For the purpose of overcoming these problems US-A-4,493,321 proposes a venous valve cutter in which the body supporting the cutting knives has been supplemented at the cutting knife end thereof with a separate leader body attached thereto in a spaced relationship by means of a thin rod, as well as with means for connecting the end of a catheter for intravenous fluid supply to be discharged at some distance from the opposite end of the cutting knives supporting body. For manoeuvring the device a flexible but torsionally rigid pulling rod is connectable to the free end of the leader body.

When using the valve cutter a distal and a proximal incision is made into either side of the vein portion to be cleaned from valves. The above mentioned pulling rod is then separately inserted through the distal incision and up along the vein until the rod end exits from the proximal incision, at which point it is attached to the cutter leader body. When the fluid supply catheter has been connected the whole assembly is then, by means of the pulling rod, slowly pulled back towards the distal incision while cutting off the venous valves passed, the fluid supplied ensuring that the valves are held completely closed during the cutting procedure and that the risk of the above mentioned spasmodic contraction of the vessel walls around the cutting body is eliminated.

Along with the relatively complex construction with several separate parts a considerable disadvantage of this device resides in the necessity of making, in addition to the distal incision, also a proximal incision into the vein, involving additional discomfort to the patient.

In EP-A1-0 248 761 another type of vein valve cutter is disclosed which also has a fluid outlet in connection with the cutting means. This vein valve cutter is in the form of a catheter, the distal end of which is provided with a plurality of cutting fingers protruding in the longitudinal direction of the catheter. The catheter is further surrounded by a telescoping sheath arranged such that it may be extended over the cutting fingers to protect the vessel walls when the catheter is advanced in the vein and be retracted and expose the cutting knives immediately prior to valve cutting. The sheath additionally has the function of defining a fluid supply channel between the sheath and the catheter, through which channel fluid may be supplied to assure closure of the valves. This vein valve cutter is primarily intended to be pushed in the vein to be cleaned, but may, e.g., for the preparation of extended vein lengths, also be pulled through the vein. For this reason the cutting end of the catheter is provided with a pulling loop, to which a pulling wire may be attached. In the last mentioned case the pulling wire will be advanced in the vein in the blood flow direction to be hooked to the catheter which is inserted through a proximal vein incision.

In addition to the fact that this vein valve cutter has a relatively complicated construction, also in this case a proximal vein incision must be made to permit the cutter to be advanced in the vein by pulling.

SUMMARY OF THE INVENTION

The object of the present invention is to provide a cutting device for venous valves, which device has at least most of the advantages of the cutting devices according to the above discussed patent specifications while at the same time having a more simple construction and not requiring the additional, proximal incision into the vein.

This object is achieved by a cutting device which has the features given in the appended claims and which is explained in more detail hereinafter.

According to a basic concept of the invention a vein valve cutting device of a type similar to, e.g., the conventional valvulotome described in the introductory part is modified by providing it, on one hand, with an internal, possibly branched duct or passage extending from a central inlet at the cutting knife end of the support member to one or more outlets on the outside of said member, and, on the other hand, with an at least slightly flexible conduit joined to said inlet and connected or connectable to a fluid supply means, such as a syringe plunger-and-cylinder unit which may be of a per se conventional type.

According to one embodiment of the invention the above mentioned duct or passage extends centrally in the support member up to the rounded insertion end thereof.

According to an alternative embodiment the fluid supply duct extends to a plurality of outlets peripherally arranged on the outside of the member, optionally in combination with an outlet at the rounded insertion end. Within the scope of this embodiment is also comprised the case that the support member completely or partially is of a porous material having such an open porosity that fluid from the central inlet may pass through the member to the outside thereof.

Preferably, the fluid supply conduit is provided with suitable marking(s) indicating the orientation of the cutting knives.

The improved cutting device according to the invention is intended to be used in a similar way as the conventional valvulotome, i.e. by inserting it through a distal vein incision and advancing it in the valve opening direction, i.e. in the normal blood flow direction of the vein, whereupon the device when drawn back in the opposite direction will cut off the venous valves by means of the cutting knives. Through the supply of physiological fluid by means of the connected fluid supply means the valves may, however, be caused to be properly stretched out in their closing state, such that they may be efficiently cut. Hereby also the above mentioned spasmodic condition of the vein is prevented, as is the risk of the cutting end getting caught in branch vessels. The embodiment having a plurality of outlets on the outside of the support member has the advantage of ensuring in all situations the provision of a fluid layer between the support member and the vessel walls to protect the latter from mechanical damage.

It is realized that no special pulling wire is required in the device but that the fluid supply conduit will perform that function.

The design and the arrangement of the cutting knife means at one end of the support member may be made in many various ways and are not critical to the invention as long as the intended valve cutting may be accomplished.

By virtue of the simple and integral construction thereof the cutting device according to the invention will be as simple to use and at least as careful to the patient as the conventional valvulotome while at the same time achieving the advantages of the more complicated device described in the above mentioned U.S. Pat. No. 4,493,321.

Hereinafter the invention will be described in more detail with regard to a preferred embodiment thereof, reference being made to the accompanying drawings, in which.

DETAILED DESCRIPTION OF THE PREFERRED EMBODIMENTS

Figure 1:
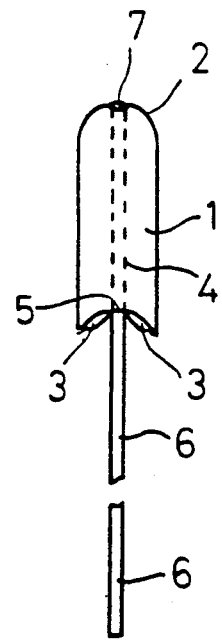
FIG. 1 is a schematic side view of an embodiment of a venous valve cutting device according to the invention.
Figure 3:
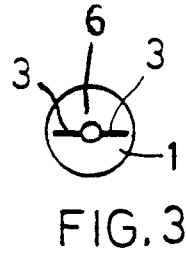
FIG. 3 is a bottom view of the embodiment of FIG. 1.
Figure 2:
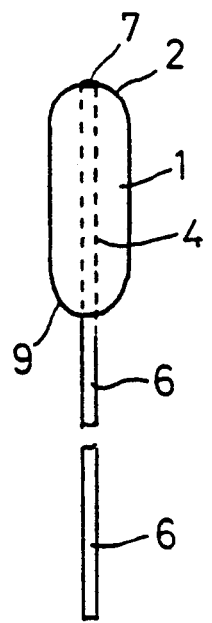
FIG. 2 is a side view perpendicular to the side view of FIG. 1.

The cutting device illustrated in FIGS. 1 and 2 consists a substantially cylindrical support member 1, which at a fore or insertion end 2 thereof is rounded in order not to damage the blood vessel walls. At the rear portion of the support member cutting knife means are provided, in the illustrated case two cutting knives 3 having cutting edges extending transversely to the longitudinal axis of the support member and substantially in the same plane. The cutting knives 3 may be separate members or integral with the support member 1. The design of the cutting knives is, however, not critical but other arrangements of cutting means may be used as well. The support member 1 is further provided with a central through-bore 4, to the rear opening 5 of which a tube 6 is connected, which may extend through the whole bore 4 up to the front orifice 7. The tube 6 is connected or arranged to be connected to a physiological fluid supply means, here a syringe plunger-and-cylinder unit 8 (FIG. 4), as will be further explained below. As shown in FIG. 2 the rear edge 9 of the support member 1 is rounded to prevent it from getting caught in branch vessels. To minimize the risk of damage to the vessel walls, as will appear from FIG. 3, the cutting knives 3 do not extend as far as to the outer periphery of the support member 1. For, e.g., a support member 1 having a diameter of about 4 mm, a suitable distance to the outer edge may be about 0.2-0.3 mm. The tube 6 is suitably provided with a marking(s) (not shown), which indicates the plane in which the cutting knives 3 are positioned, e.g., line-markings.

Figure 4:
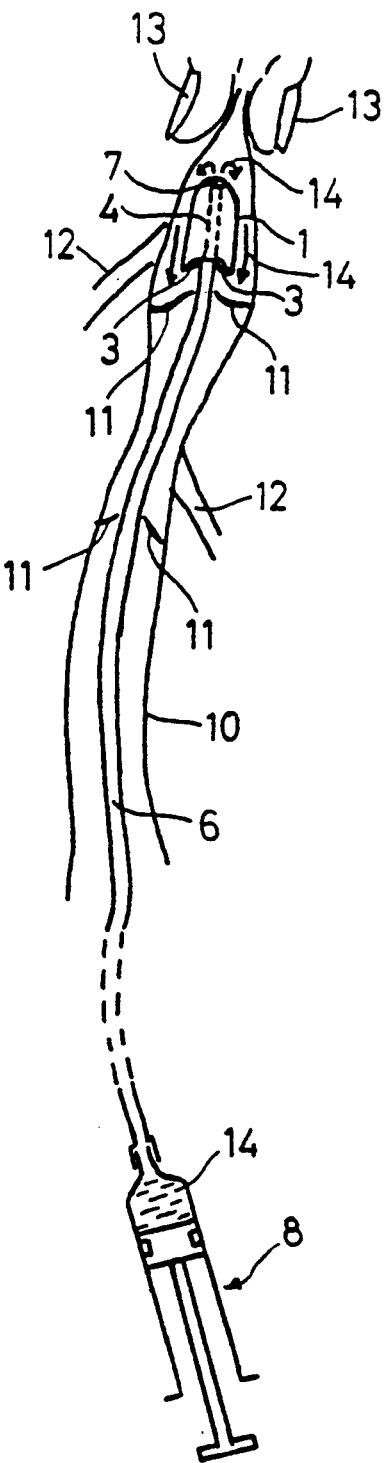
FIG. 4 is a schematic illustration of the cutting device of FIGS. 1-3 in use inserted into a vein.

In FIG. 4 the cutting device is shown inserted into a superficially located vein 10, whose valves 11 are to be removed. To insert the device into the vein the branch vessels 12 thereof are tied off and a distal incision is made either into the vein itself or into a branch vessel, and the support member 1 is then advanced the desired distance in the passage direction of the valves 11 (i.e. the normal blood flow direction of the vein) by means of the tube 6 under assistance by the fingers, indicated with the reference numeral 13. If not already done previously, the tube 6 is then connected to the syringe unit 8. The vein 10 is subsequently pinched with the fingers 13, just above the free end of the support member 1, whereupon physiological fluid 14 by means of the syringe unit 8, via the tube 6 and the bore 4, is injected into the space defined between the pinched area and the vein valve 11 located immediately behind the cutting knives 3 in a sufficient volume for the vein valve in its capacity as a non-return valve to be properly stretched. When the support member 1 is drawn back by means of the tube 6 the valve 11 is efficiently cut by the cutting knives 3. One then proceeds in the same way until all the valves 11 of the vein portion in question have been cut, and the support member 1 is then removed through the above mentioned distal incision.

Figure 5:
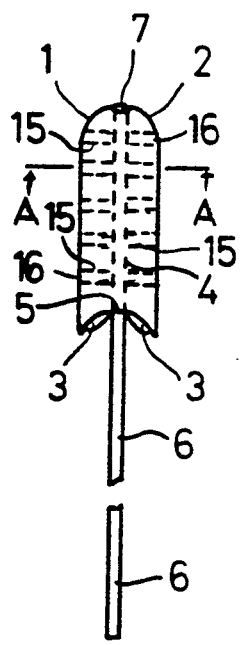
FIG. 5 is a side view of an alternative embodiment of the venous valve cutting device according to the invention.
Figure 6:
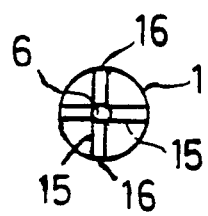
FIG. 6 is a sectional view along A'A in FIG. 5.

In FIG. 5 and 6 an alternative embodiment of the invention is illustrated in which the bore 4 has been provided a number of branchings 15 ending in outlets 16 on the outside of the support member 1, in the illustrated case five branching points each of which is connected to four outlets. Since the fluid is supplied to the outside of the support member 1 also in this way, there is always assured a lubricating fluid layer around the entire support member and thereby protection of the vessel walls against mechanical abrasion. Such supply of fluid to the periphery of the support member 1 could also be achieved with the cutting device according to FIG. 1-3 if the support member thereof were made of a porous material having a sufficient open porosity.

The invention is, of course, not restricted to the embodiments particularly described above and shown in the drawing, but many variations and modifications are possible within the scope of the inventive concept and the following claims.

I claim:

1. A device for cutting venous valves, comprising a support member (1), adapted to be inserted into a vein and having a fore, rounded insertion end (2) and a rear end, cutting means (3) provided at said rear end for cutting venous valves when the support member (1) is moved backwards in the vein, and means for supplying fluid into the vein to close the valves to be cut, characterized in that said fluid supplying means comprise a branched fluid duct system (4) provided in the support member (1) and extending from a fluid inlet (5) centrally disposed at the cutting means end thereof to a plurality of fluid outlets (7; 16) arranged peripherally and along the support member (1) to ensure a fluid layer around the entire support member (1) and an at least slightly flexible conduit (6) joined to said fluid inlet (5) and connected or connectable to a fluid supply (8), said conduit (6) serving as a pulling means.

2. A device according to claim 1, characterized in that said fluid duct system (4) comprises at least one outlet at the fore, insertion end (2) of the support member (1).

3. A device according to claim 1 or 2 characterized in that the support member (1) at least partially is porous, the pore system thereof defining at least part of said fluid duct system.

4. A device according to any one of claim 1 or 2, characterized in that said fluid supply is a syringe plunger-and-cylinder unit (8).

5. A device according to any one of claims 1 or 2 characterized in that said fluid supply conduit (6) is provided with a marking(s) indicating the orientation of the cutting means plane or planes.

6. A device according to claim 4, characterized in that the support member (1) at least partially is porous, the pore system thereof defining at least part of said fluid duct system.

7. A device according to claim 5, characterized in that the support member (1) at least partially is porous, the pore system thereof defining at least part of said fluid duct system.

8. A device according to claim 5, characterized in that said fluid supply is a syringe plunger-and-cylinder unit (8).

* * * * *